United States Patent
Perret, Jr.

[11] Patent Number: 5,542,844
[45] Date of Patent: Aug. 6, 1996

[54] DISPOSABLE ORTHODONTIC BRACKET PAD

[76] Inventor: Gerard A. Perret, Jr., 15205-3 Plantation Oaks Dr., Tampa, Fla. 33647

[21] Appl. No.: 322,946

[22] Filed: Oct. 13, 1994

[51] Int. Cl.⁶ ................................................. A61C 7/16
[52] U.S. Cl. ................................................................ 433/9
[58] Field of Search .................... 40/156; 43/114; 206/0.83, 0.84, 63.5, 460, 489, 562, 563, 564; 433/2, 8, 9, 25

[56] References Cited

U.S. PATENT DOCUMENTS

| | | | |
|---|---|---|---|
| 276,844 | 5/1883 | Manahan | 43/114 |
| 509,546 | 11/1893 | Muller | 206/0.83 |
| 3,023,539 | 3/1962 | Emerson, Jr. | 43/114 |
| 3,245,523 | 4/1966 | White | 206/0.83 |
| 4,480,399 | 11/1984 | Teti, Jr. | 40/594 X |
| 4,979,611 | 12/1990 | Boliger et al. | 206/460 X |

Primary Examiner—Robert P. Swiatek
Assistant Examiner—Yvonne Abbott
Attorney, Agent, or Firm—Dominik & Stein

[57] ABSTRACT

A disposable orthodontic bracket pad. The bracket pad comprises a top and a bottom sheet, wherein the top sheet is made of an inexpensive liquid-impermeable material and has a plurality of openings defining bracket staging areas, and a bottom sheet made of an inexpensive material having one side coated with an adhesive material. The bracket staging areas are preferably arranged in the shape of an arch to mimic the arrangement of teeth and facilitate bracket identification. The bottom sheet is adhered to the top sheet via said adhesive materials, forming a bracket pad having adhesive bracket staging areas. The bracket pad is preferably less than ⅛ of an inch in thickness.

15 Claims, 1 Drawing Sheet

DISPOSABLE ORTHODONTIC BRACKET PAD

BACKGROUND OF THE INVENTION

1. Field of the Invention

The present invention concerns an organizing device, and in particular, an organizing device which is particularly suited for organizing brackets and the bonding material used in orthodontic treatment, and optional enhancements of said device.

2. Description of the Related Art

During the course of orthodontic treatment, small brackets are attached to a patient's teeth. The purpose of these brackets is to transfer the forces from the orthodontic wires, springs, rubber bands, and other assorted attachments to the teeth.

In any one patient's mouth, the individual teeth are formed in various sizes, shapes, and contours. Since the orthodontic brackets are essentially cemented to the teeth, it is desirable to have the base of the bracket shaped and contoured to adapt as closely as possible to the surface of the particular tooth to which it will be bonded. Thus, on any given patient, an orthodontist may have as many differently designed brackets to bond as there are teeth.

Manufacturers of orthodontic brackets often ship the brackets in bulk, where like brackets are packaged together. When a patient is scheduled to have braces put on, it is then necessary for the orthodontist, or one of his employees, to remove one of each type of bracket to be utilized on that particular patient, and to organize and arrange those brackets so that they may be efficiently retrieved when needed.

Such efficiency requires that the brackets be arranged so that an orthodontist or his assistant is able to glance at the set of brackets and immediately know which bracket corresponds to any given particular tooth. In addition, each bracket must be held in a particular orientation such that, when picked up by the assistant with the appropriate orthodontic instrument, the base of the bracket is exposed and available for application of the cement, or bonding material.

In addition to organizing the required brackets, it is also necessary to have the bonding material ready for use. This requires removing a small amount of the material from the bulk packaging in which it is purchased, and placing the material to be used on an appropriate, clean surface, until such time that it is required for application to the bracket.

Several products currently exist on the market for organizing brackets and bonding materials. They all consist of a thin sheet of plastic with small openings cut into the material. The openings are aligned in two rows, each row with the same number of openings. Affixed to the undersurface of the plastic sheet is a strip of tape or other material with an adhesive on one surface. The strip is oriented such that the adhesive surface sticks to the undersurface of the plastic sheet and completely covers the openings mentioned above. When the sheet is laid on a flat surface, one sees two rows of small adhesive circles showing through the plastic material. Each opening is sized appropriately for one bracket, and each row of openings is designed to hold enough brackets for either the upper or the lower teeth. This product is often called a "bracket pad".

Thus the brackets for the upper teeth would be placed on the first row of adhesive circles, and the lower brackets on the second row. The brackets on the left side of the pad will correspond to the teeth on the patient's left, and the brackets on the right side of the pad will correspond to the teeth on the patient's right. Additionally, the adhesive circles are usually numbered to correspond with particular teeth. The adhesive strip not only serves to hold the brackets in place while transferring the brackets to the treatment area, but it keeps the brackets in the proper orientation for efficient removal and application of cement.

In addition to the bracket organizing aspects of the currently available products, many of them also incorporate a method of organizing the bonding material. This method usually involves small depressions in a portion of the plastic sheet that has been formed to rise above the level of the adhesive circles. These depressions can hold small quantities of the bonding materials in either liquid or paste forms.

Additional products exist specifically for use in organizing the bonding materials alone, with no mechanism for organizing and/or orienting orthodontic brackets. Such products are usually in the form of a small sheet of paper or cardboard wherein one surface of the sheet is treated and/or manufactured as to be essentially impermeable and nonabsorbent to liquids. Said sheets are then stacked and bound in stack form on one edge to create a pad of multiple sheets for efficient packaging and storage. When it is necessary to prepare the materials for the procedure of bonding brackets to teeth, the top sheet is removed for use, and the necessary amounts of bonding materials are placed on the treated surface. Such products are often called "mixing pads".

The available products are intended to be disposable. Thus each bracket pad would be used to hold the brackets necessary for one patient. Each mixing pad would hold the bonding materials necessary for one patient. Following the bracket placement procedure, the pads should be disposed of, thus eliminating the need for sterilization before use with another patient.

The available products, however, have practical deficiencies. One such deficiency involves the method of organizing the bonding material. The current bracket pad design is acceptable for materials that do not require mixing prior to use. Many bonding materials used in orthodontics, however, require the mixing together of two fluid or paste components immediately prior to placement on the tooth or bracket. With the current bracket pads, these materials would need to be removed from their holding areas on the bracket pad and mixed together. This additional step causes additional costs due to excess waste of material and the requirement of an additional surface, such as a mixing pad, on which to perform the mixing procedure. Orthodontists employing such bonding materials often place theses materials directly onto the mixing pad surface, bypassing the bracket pad altogether. They thereby avoid the waste of materials, but the additional bonding material organizing feature designed into the bracket pad then becomes superfluous.

A second deficiency associated with the currently available bracket pads is their cost. The manufacturing process necessary to mold and stamp the plastic sheets is relatively costly when compared to that of other disposable products. While these products are designed to be disposable, many orthodontists consider them too expensive to dispose of following each procedure. The bracket pads are often used on several different patients before disposal. Thus, in practice, the currently available bracket pads are not a disposable product, notwithstanding such claims by the manufacturers.

The third disadvantage of the presently available bracket pads follows from the second disadvantage: Since the manufacturers claim that their products are disposable, they do not design them to be sterilized by currently available sterilization techniques. Since many end users consider the products to be too expensive for disposal after a single use, they use the product on several different patients before disposal. This situation creates obvious cross-contamination concerns.

A fourth disadvantage associated of the presently available bracket pads involves the alignment of the openings designed for each bracket. In all presently available products, the bracket holding areas are arranged such that the brackets will be in two straight rows, one for the upper brackets, and one for the lower brackets (as previously described.) It is difficult for a newly hired trainee to visualize which bracket on the pad correspond to which tooth in the mouth. It is also difficult for an orthodontist to oversee the job being performed by his assistant, since it may be difficult to "read" the bracket pad at a glance. The teeth in the mouth are obviously not arranged in a straight line. This increases the likelihood of an assistant handing an incorrect bracket to the orthodontist during the bonding procedure.

Accordingly, each of the bracket pads presently available for use in organizing orthodontic brackets and bonding materials prior to use have a number of deficiencies. There remains in the trade a need for a lightweight, cost-effective, efficiently designed, sufficiently non-liquid-permeable, disposable orthodontic bracket pad which poses no risk of cross-contamination, provides the necessary bracket organization and orientation, and allows for use, without an additional mixing pad, of orthodontic bonding materials, regardless of the necessity, or lack thereof, to mix said bonding materials together prior to use.

SUMMARY OF THE INVENTION

After investigation and experimentation, the present inventor has discovered that all of the above-elaborated deficiencies can be overcome by a thin, flat disposable bracket pad having a mixing pad feature, so that the same pad can be used to both stage the orthodontic brackets and ready the bonding materials.

In a preferred embodiment the disposable bracket pad comprises two sheets, a top sheet and a bottom sheet. The top sheet, at least the upper surface of which is liquid impermeable, is provided with through-holes or openings to define bracket staging areas. The bottom sheet is made of a material treated on the upper surface with a tacky adhesive material and oriented such that the upwards facing adhesive material of the bottom sheet is accessible through the openings in the top sheet. The bracket pad has properties as discussed below.

An important feature of the present invention is that the bracket pad comprises a two layered sheet made of inexpensive materials and methods designed to produce a single-use, disposable pad.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other bracket pads for carrying out the same purposes of the present invention. It should also be realized by those skilled in the art that such equivalent structures do not depart from the spirit and scope of the invention as set forth in the appended claims.

BRIEF DESCRIPTION OF THE DRAWING

For a fuller understanding of the nature and objects of the present invention, reference should be made to the following detailed description in conjunction with the accompanying drawings wherein.

DESCRIPTION OF THE PREFERRED EMBODIMENTS

In a preferred embodiment the disposable bracket pad comprises two sheets, a top sheet and a bottom sheet.

The top sheet, at least the top surface of which is liquid impermeable, is provided with through-holes or openings to define bracket staging areas. The areas of the top sheet which are not provided with openings provide a smooth even surface.

The top sheet may be made of a paper product such as a liquid-impermeable paper or cardboard, or any other material which has been treated with a liquid impermeable substance to render it impermeable. The term "liquid impermeable" is intended to mean that a surface is provided which is sufficiently resistant to the bonding materials used in the process of adhering brackets to teeth so that the top sheet does not absorb bonding materials or deteriorate during the process of preparing the bonding materials and adhering brackets to teeth. The term "bonding material" is intended to mean any liquid or paste or other material used in the bonding process, i.e., solvents, cleaners, surface preparatives, adhesives, etc. The top sheet is preferably made of treated paper, but may be made of plastic (e.g., a high density polyethylene copolymer, a polyolefin such as polypropylene and polyethylene, polyethylene terephthalate, polystyrene, acrylonitrilestyrene-butadiene polymer, nylon, acetal polymer, polycarbonate, nitrile resins, polyvinyl chloride, polysulfone and other semi-rigid to rigid polymers including multipolymers, polymer blends and polymer laminar constructions, a vinyl such as polyvinyl chloride, a styrene such as high impact polystyrene, an acrylic, an olefin, etc.), cardboard, or any other material through which small openings can be fashioned without compromising the integrity of the material. Particularly preferred materials include those used in any of the liquid-impermeable mixing pads currently on the market.

The preferred shape of the top sheet is rectangular with dimensions of 2 ⅞ inches by 3 ⅛ inches. Larger dimensions are suitable, particularly for increasing the size of the mixing pad area, or if additional openings are desired for additional or extra brackets. Such optional increases in size are balanced by the need to maintain a size which is economical and with which storage space does not become a concern. Smaller dimensions are also possible, particularly where a smaller number of bracket staging areas are selected.

Figure 1:
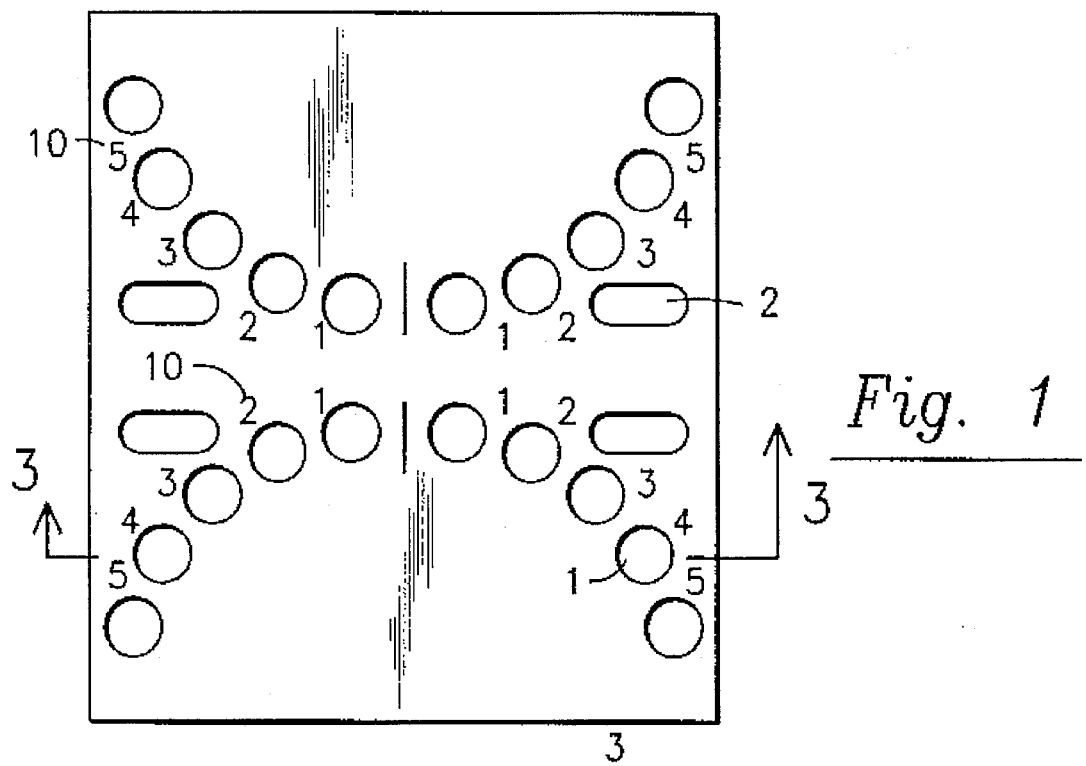
FIG. 1 is a top view of a first embodiment of the disposable orthodontic bracket pad, showing an arch shaped arrangement of bracket staging areas.
Figure 2:
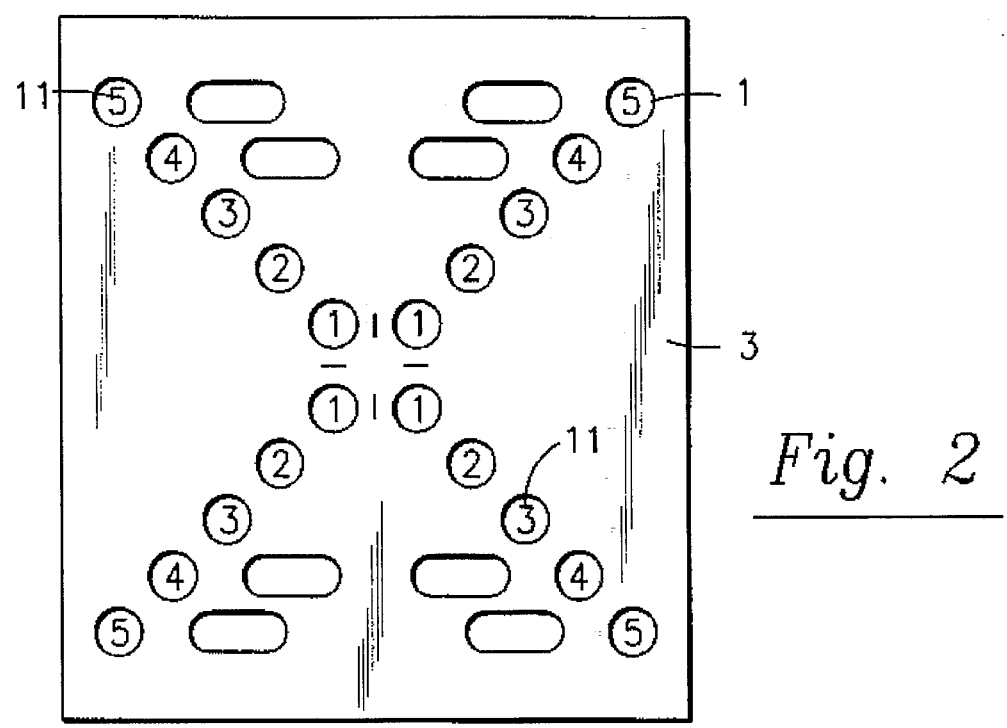
FIG. 2 is a top view of a second embodiment of the disposable orthodontic bracket pad, showing a "V" shape arrangement of bracket staging areas.

The size, shape, and geometry of the bracket staging areas is not particularly limited, but the areas are preferably laid out in a pattern mimicking the arrangement of the teeth in the mouth. An illustrative embodiment is shown in FIGS. 1 and 2. The number of openings 1, 2 in the top sheet 3 of the most preferred embodiment of the bracket pad of the present invention is 24 (as shown in FIG. 1). Of these, 20 openings 1 are circular in shape with a diameter of approximately ¼th of an inch. The remaining openings 2 are oblong in shape with dimensions of approximately ³⁄₁₆ths of an inch by ⁷⁄₁₆ths of an inch, with rounded corners. The circular openings are preferably arranged in two distinct arch shaped configurations of 10 openings each, where the orientation of the arch forms to each other is as shown in FIG. 1.

The number of openings is variable for additional or extra brackets as may be desired. Since the normal human anatomy provides 32 teeth, a reasonable upper limit on the number of openings would be 32. It is also acceptable to decrease the number as well. If only a few teeth are to be bracketed in a given procedure, it would be wasteful to use a pad large enough for 20 brackets or more. A bracket pad of 10 circular openings plus 2 oblong openings could be designed, with one arch form, to be half the size of the full bracket pad. Fewer than six openings, although possible, would jeopardize the conceptualization of an arch form and may lead to confusion as previously discussed. It also may not be economical.

As is apparent from the above discussion, the bracket staging areas are most preferably of a sufficient number to accommodate all of the orthodontic brackets that might be needed on any one particular patient, one bracket staging area being provided for each tooth which may require a bracket. To use, the brackets are selected, properly oriented, and prestaged by placing directly onto the staging areas. In a more preferred embodiment of the invention, numbers 10, 11 which in orthodontic convention represent specific teeth are preprinted inside 11, or preferably adjacent to 10, the respective bracket staging areas for error free correlation between the bracket in staging area.

The size of the openings may be increased or decreased as well. Orthodontic brackets are manufactured in different sizes and designs for a variety of reasons dealing with the intricacies of orthodontic tooth movement. Larger openings may be desired for certain bracket types. Since larger openings would require larger, bulkier pads, ½ inch diameter would be a reasonable upper limit. Openings too small to accommodate the bases of the brackets would of course be self-defeating. A reasonable lower limit would be ⅛th of an inch diameter.

The shapes of the openings may also vary, as some brackets have square bases, some round, and others rectangular, as dictated by the bracket manufacturers. The variety of shapes that could be employed for the purposes of the present invention are limited only in that they should allow for a bracket of a known size to fit therein.

The arch geometry (FIGS. 1, 2) is also variable, considered either individually or considering the relationship of each of the arches to the other. As they are related to each other, any arrangement that would allow sufficient space of the upper sheet for use as a mixing pad is sufficient. In addition, each arch may be flattened, broadened, more v-shaped (FIG. 2), more square shaped, wider spaced between openings, etc., provided that sufficient space remains open for readying bonding materials.

The bottom sheet may be made of any material, and is preferably made of any paper or plastic material usually used as a backing for tapes. The upper surface of the bottom sheet is treated with a tacky adhesive material and oriented such that the upwards facing adhesive material of the bottom sheet is accessible through the openings in the top sheet. The adhesive material of the bottom sheet is used not only to hold brackets through the openings in the top sheet, but also to adhere the bottom sheet to the bottom surface of the top sheet, with portions of the adhesive material of the bottom sheet being exposed through the openings of the top sheet.

The adhesive material may be any pressure-sensitive adhesive material that is sufficiently tacky to hold the largest and heaviest orthodontic bracket available on the market, even if the bracket pad were turned upside down. The adhesive material may be obtained by, e.g., blending a natural or synthetic rubber with a resin bonding agent, or by copolymerizing an acrylic monomer such as an acrylic acid ester and one or more unsaturated monomer having one or more polar group, such as a carboxyl or epoxy group, followed by copolymerizing and cross-linking the copolymer. The adhesive is preferably a pressure-sensitive adhesive acrylic solid elastomer blend, as conventionally used in "masking tape", and which does not readily harden or solidify when exposed to the atmosphere. A preferred acrylic solid elastomer blend is an acrylic ester copolymer. Comonomers utilized have functional groups such as glycidyl, methylol or carboxylic acid groups combined with a functional group containing reagents such as an epoxy resin, a polyisocyanate or a formaldehyde condensation resin.

The size and shape of the lower sheet is only relevant in that it must be sufficient to completely cover all openings in the top sheet such that the adhesive material is accessible through said openings.

Figure 3:
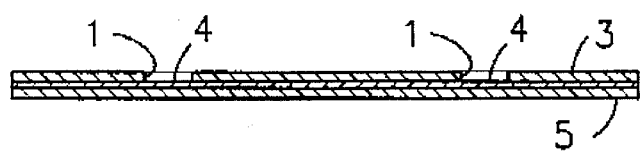
FIG. 3 is an enlarged side view of the embodiment of FIG. 1.

As seen in FIG. 3, the adhesion of the top sheet 3 to the bottom sheet 5 forms a bracket pad having slightly recessed areas 1 with an upward facing adhesive surface 4 for staging brackets, preferably yielding a total bracket pad thickness no greater than ⅛th of an inch, more preferably not greater than ¹⁄₁₆th of an inch, and most preferably between about ¹⁄₃₂nd and ¹⁄₁₆th of an inch. While it is possible to make bracket pads of less than ¹⁄₃₂nd of an inch, the most readily available and economical materials lend themselves to the making of bracket pads of between ¹⁄₃₂nd and ¹⁄₁₆th of an inch. The bracket pad of the present invention is of sufficient stiffness to support the weight of the number of brackets it is designed to hold without folding.

The bracket pad according to the present invention can easily be mass manufactured by the steps of (1) obtaining a continuous roll of a material suitable for forming a top sheet, (2) stamping, punching, cutting, or otherwise forming the appropriate openings in the top sheet, (3) obtaining a continuous roll of a material of which one side is treated with a pressure-sensitive adhesive material as discussed above, (4) continuously running said top and bottom sheets together so said bottom sheet adheres to said top sheet, and so that adhesive material of the bottom sheet is displayed through the open areas of the top sheet to define the bracket staging areas, and (5) cutting the thus formed continuous pad into individual pads.

An advantage of the present invention is that the staging areas are arranged in a fashion that leaves significant portions of the surface area of the liquid-impermeable upper sheet available for mixing or preparing the bonding materials. The portion of the liquid impermeable surface of the upper sheet not associated with adhesive exhibiting staging areas is designed to be used as a mixing surface. The surface is flat; there are no raised or depressed areas on the surface of the pad designed to hold bonding materials. The bonding materials are simply extruded or placed on the upper surface of the upper sheet of the pad in an area not provided with bracket staging areas. When using bonding materials that require mixing immediately prior to use, the materials are simply deposited next to each other and left until they are ready to be mixed together. This eliminates the need for an additional mixing surface.

A further advantage of the present invention is that the staging areas are also arranged in a fashion to mimic the arrangement of the teeth in the mouth. For example, teeth in the mouth are generally arranged in the form of an arch. Arranging the staging areas on the bracket pad in arch form, one arch for the upper brackets and one arch for the lower brackets, would minimize the confusion associated with learning which bracket corresponds to which tooth, and would facilitate the identification and selection of the proper bracket even by the trained assistant or orthodontist.

Another advantage of the present invention is that the bracket pad once formed, without raised areas, may be stacked one on top of the other forming a stack of bracket pads. A preferred method of selling the present bracket pad would be in the form of stacked packets. The stack of bracket pads may be designed to meet the various quantity needs of the orthodontist. The bracket pads, stacked on top of each other and preferably connected together along an edge by some form of rubber-like adhesive, form a packet of bracket pads. The adhesive is of the type used in note pads, tear-off memo pads, etc, releasably adhering bracket pads to each other along one edge such that said pads are held in a stack prior to use, and are rendered useable by peeling individual bracket pads from the stack. This type of adhesive is a well known art form and a detailed description is not necessary.

As discussed above, a product is only disposable if the consumer actually throws it away after use. While available bracket pads are marketed as "disposable", they are rarely disposed of after a single use due to their cost and their reusability. The present invention is constructed with inexpensive materials and designed in a manner that would keep production cost down. Once the brackets have been removed and placed on the patient's teeth, the bracket pad of the present invention will, in practice, actually be disposed of due to the significantly low cost per pad paid by the consumer.

An additional reason that the pad will be discarded is that many of the bonding materials cannot be re-used, particularly those that require mixing. Therefore, the mixing pad feature of the present invention also enhances the likelihood of single-patient use, thereby eliminating the risk of cross-contamination.

Yet a further advantage resulting from this construction is that a single bracket pad is used for both mixing and staging where previously two items (bracket holder and mixing pad) were required, so that less storage space is taken up, utilization is more convenient, and costs are reduced.

Further yet, it is possible to provide the surface of the pad with an area which can be readily marked on with a pen, a pencil, or a grease pencil, in order to identify the patient for whom the brackets are intended. Since the bracket pad will actually be discarded after use, the consumer will more readily mark on the bracket pad. The identification of the patient on the bracket pad will also comfort the patient, since the patient will feel that the pad is personal and is not being reused.

A further benefit of the bracket pad, and particularly of the bracket pad with marking areas, is the ability to set up brackets for a number of patients in advance, e.g., to stage all the brackets for all patients for a given day.

Accordingly, when considering the advantages of the invention, the bracket pad of the present invention far exceeds any existing product in economy, consumer friendliness, and ease of manufacture. It is a totally new bracket pad designed to combine and solve the specific problems of bonding material management, bracket organization and orientation, time management in the orthodontic bonding process, manufacturing cost, cost-effectiveness, thus encouraging disposal and minimizing the risk of cross-contamination. No product presently on the market satisfies all these requirements.

Although this invention has been described in its preferred form with a certain degree of particularity with respect to organizing orthodontic brackets and bonding materials, it is understood that the present disclosure of the preferred form has been made only by way of example and that numerous changes in the details of structures and the composition of the involved materials may be resorted to without departing from the spirit and scope of the invention.

Now that the invention has been described,
What is claimed is:

1. A disposable orthodontic bracket pad comprising:
   a top sheet having an upper surface and a lower surface, at least the upper surface of which is liquid impermeable, said top sheet provided with a plurality of openings defining bracket staging areas and provided with an area for mixing orthodontic bonding materials; and
   a bottom sheet having an upper surface and a lower surface and having a pressure-sensitive adhesive material disposed only on the upper surface thereof, said bottom sheet being adhered to said top sheet via said pressure sensitive adhesive material such that said adhesive material of said bottom sheet is exposed through said openings in said top sheet to form adhesive areas for staging brackets.

2. A disposable orthodontic bracket pad as in claim 1, wherein said top sheet is made of a plastic.

3. A disposable orthodontic bracket pad as in claim 1, wherein said top sheet is made of a treated cardboard.

4. A disposable orthodontic bracket pad as in claim 1, wherein said bracket pad is flat and not more than ⅛th of an inch thick.

5. A disposable orthodontic bracket pad as in claim 1, wherein said bracket pad is flat and not more than 1/16th of an inch thick.

6. A disposable orthodontic bracket pad as in claim 1, wherein said bracket pad is flat and not more than 1/32nd of an inch thick.

7. A disposable orthodontic bracket pad as in claim 1, wherein said bottom sheet is masking tape.

8. A disposable orthodontic bracket pad as in claim 1, wherein said bottom sheet is cellophane tape.

9. A disposable orthodontic bracket pad as in claim 1, further comprising an area on the upper surface of the top sheet of the bracket pad receptive to marking with a writing instrument.

10. A disposable orthodontic bracket pad as in claim 1, said bracket pad being provided with pre-printed numbers adjacent to said bracket staging areas.

11. A disposable orthodontic bracket pad as in claim 1, said bracket pad being provided with pre-printed numbers within said bracket staging areas.

12. A disposable orthodontic bracket pad comprising a top sheet having an upper surface and a lower surface, at least the upper surface of which is liquid impermeable, said top sheet provided with a plurality of openings defining bracket staging areas and provided with an area for mixing orthodontic bonding materials; and a bottom sheet having an upper surface and a lower surface and having a pressure-sensitive adhesive material disposed on the upper side thereof, said bottom sheet being adhered to said top sheet via said pressure sensitive adhesive material such that said adhesive material of said bottom sheet is exposed through said openings in said top sheet to form adhesive areas for staging brackets;

wherein said bracket staging areas are arranged in the shape of an arch.

13. A disposable orthodontic bracket pad comprising a top sheet having an upper surface and a lower surface, at least the upper surface of which is liquid impermeable, said top sheet provided with a plurality of openings defining bracket staging areas and provided with an area for mixing orthodontic bonding materials; and a bottom sheet having an upper surface and a lower surface and having a pressure-sensitive adhesive material disposed on the upper side thereof, said bottom sheet being adhered to said top sheet via said pressure sensitive adhesive material such that said adhesive material of said bottom sheet is exposed through said openings in said top sheet to form adhesive areas for staging brackets;

wherein said bracket staging areas are arranged in the shape of a "V".

14. A multiple bracket pad assembly comprising a plurality of disposable orthodontic bracket pads in a stack, each of said disposable orthodontic bracket pads comprising a top sheet having an upper surface and a lower surface, at least the upper surface of which is liquid impermeable, said top sheet provided with a plurality of openings defining bracket staging areas and provided with an area for mixing orthodontic bonding materials; and a bottom sheet having an upper surface and a lower surface and having a pressure-sensitive adhesive material disposed on the upper side thereof, said bottom sheet being adhered to said top sheet via said pressure sensitive adhesive material such that said adhesive material of said bottom sheet is exposed through said openings in said top sheet to form adhesive areas for staging brackets;

wherein said stacked disposable orthodontic bracket pads are releasably adhered to each other such that said pads are held in a stack prior to use, and are rendered useable by peeling one bracket pad from the stack.

15. A disposable orthodontic bracket pad comprising:

a top sheet provided with a plurality of openings defining bracket staging areas, said bracket staging areas being arranged so as to form at least one arch; and a bottom sheet made of a material and having a pressure-sensitive adhesive material disposed on the upper side thereof, said bottom sheet being adhered to said top sheet via said pressure sensitive adhesive material such that said adhesive material of said bottom sheet is exposed through said openings in said top sheet to form adhesive areas for staging brackets.

* * * * *